United States Patent
Eliasson et al.

(10) Patent No.: US 10,569,009 B2
(45) Date of Patent: Feb. 25, 2020

(54) MOTORIZED CATHETER SYSTEM WITH IMPROVED INFLATION CONTROL

(71) Applicant: DENTSPLY IH AB, Mölndal (SE)

(72) Inventors: Göran Eliasson, Stenungsund (SE); Andrea Schmid, Mölnlycke (SE); Kjell Wellenstam, Askim (SE)

(73) Assignee: DENTSPLY IH AB, Mölndal (SE)

( * ) Notice: Subject to any disclaimer, the term of this patent is extended or adjusted under 35 U.S.C. 154(b) by 261 days.

(21) Appl. No.: 15/847,577

(22) Filed: Dec. 19, 2017

(65) Prior Publication Data

US 2018/0177937 A1  Jun. 28, 2018

(30) Foreign Application Priority Data

Dec. 22, 2016 (EP) .................................. 16206373

(51) Int. Cl.
*A61M 29/00* (2006.01)
*A61M 3/02* (2006.01)
*A61M 25/10* (2013.01)

(52) U.S. Cl.
CPC ........ *A61M 3/0295* (2013.01); *A61M 3/0258* (2013.01); *A61M 25/10184* (2013.11);
(Continued)

(58) Field of Classification Search
CPC .......... A61M 2205/502; A61M 3/0258; A61M 3/0295; A61M 2205/50; A61M 2210/1067; A61M 25/10187; A61M 3/2095; A61M 25/10184; A61M 25/1018; A61M 25/1081; A61M 25/10; A61M 16/044; A61F 5/442; A61F 5/44; A61B 90/02
See application file for complete search history.

(56) References Cited

U.S. PATENT DOCUMENTS

| | | |
|---|---|---|
| 7,914,505 B2 | 3/2011 | Moeller-Jensen et al. |
| 2014/0052063 A1 | 2/2014 | Gregory et al. |

(Continued)

FOREIGN PATENT DOCUMENTS

| | | |
|---|---|---|
| EP | 2683424 | 7/2015 |
| WO | 2010077340 | 7/2010 |

(Continued)

OTHER PUBLICATIONS

European Search Report for European Patent Application No. 16206373.9, dated Jun. 19, 2017 (9 pages).

*Primary Examiner* — Rebecca E Eisenberg

(74) *Attorney, Agent, or Firm* — Perkins Coie LLP

(57) ABSTRACT

Methods and systems for automated control of the inflation of an inflatable retention member, e.g. a balloon, in a catheter are disclosed. One catheter is preferably a rectal or anal catheter, and the inflation is controlled by a controller. A plurality of predetermined inflation levels are provided, and for each of level, a pumping time threshold and a pressure level threshold are defined. The pressure in the balloon is continuously measured during the inflation. An inflation level is selected form said plurality of inflation levels, and an electric pump is used to inflate the inflatable retention member. Operation of the electric pump is continued until one of the pumping time threshold and pressure level threshold of the selected inflation level has been reached.

17 Claims, 7 Drawing Sheets

(52) U.S. Cl.
CPC . *A61M 25/10181* (2013.11); *A61M 25/10185* (2013.11); *A61M 2205/3331* (2013.01); *A61M 2205/3344* (2013.01); *A61M 2205/50* (2013.01); *A61M 2205/502* (2013.01); *A61M 2205/8206* (2013.01); *A61M 2210/1064* (2013.01); *A61M 2210/1067* (2013.01); *A61M 2210/1089* (2013.01)

(56) References Cited

U.S. PATENT DOCUMENTS

| | | | |
|---|---|---|---|
| 2015/0335529 A1 | 11/2015 | Andersson et al. | |
| 2016/0058987 A1* | 3/2016 | Korman | A61M 29/02 606/192 |
| 2016/0114148 A1 | 4/2016 | Holm et al. | |
| 2016/0193403 A1 | 7/2016 | Andersson | |

FOREIGN PATENT DOCUMENTS

| | | |
|---|---|---|
| WO | 2012120456 | 9/2012 |
| WO | 2014154635 | 10/2014 |
| WO | 2016095929 | 6/2016 |

* cited by examiner

MOTORIZED CATHETER SYSTEM WITH IMPROVED INFLATION CONTROL

CROSS-REFERENCE TO RELATED APPLICATIONS

This patent document claims the benefits and priority to European Patent Convention Application No. 16206373.9, filed on Dec. 22, 2016, which is incorporated herein by reference in its entirety.

TECHNICAL FIELD

The disclosed embodiments relate to catheter systems, and in particular to an irrigation system for rectal and/or stomal irrigation, and suitable for self-administration of an irrigation liquid. The disclosed embodiments also relate to a method for automated control of inflation of an inflatable retention member in a catheter.

BACKGROUND

Catheters and catheter systems are used for many types of medical procedures. In some catheter systems, the catheters are provided with retention members, to retain the catheters in place during use when inserted into the patient's/user's body. A common type of retention member for such catheters is an inflatable retention member, such as an inflatable balloon, arranged close to the insertable end of the catheter. A separate lumen is arranged within the catheter for transferring an inflation fluid from an external source, through the length of the catheter, and into the inflatable retention member for inflation, and for transferring the inflation fluid back though the length of the catheter during deflation of the inflatable retention member. The inflatable retention member is inflated to a suitable diameter with fluid, such as air, water or saline.

In addition to the lumen used for the inflation fluid, a second lumen may be provided to deliver e.g. irrigation fluid to the body cavity, for drainage of a liquid or the like, such as faeces in case of a rectal catheter or urine in case of a indwelling urinary catheter, from the body cavity, etc.

The inflatable retention member preferably surrounds the distal end of the catheter and preferably has a toroidal shape when fully inflated.

However, systems using an inflatable retention member must be used carefully because they can create too much pressure on the body rectal tissue if the retention balloon is over inflated. Accordingly, all such catheter systems must have an indicated maximum volume for the retention balloon that each manufacturer has established as safe. However, this maximum volume can be exceeded by over inflating the inflatable retention member, resulting in damage to the soft tissue surrounding the retention member. In particular, over inflation to such a level that the inflatable retention member explodes may be both harmful and painful, and may in severe cases even have lethal consequences. However, even without exploding, the inflated retention member can create discomfort, pain or even damage by creating too much pressure on the tissue in vicinity of the inflatable retention member.

Various attempts have been made over the years to propose solutions to better control the inflation of such inflatable retention members. However, most of these proposed solutions are very complex and costly to produce. Further, these known systems are still not able to provide the user with adequate possibilities to control the inflation, and at the same time ensuring that over inflation is avoided.

For example, US 2016/193403 by the same applicant discloses an irrigation system in which balloon inflation is controlled in accordance with pre-set inflation levels. However, the inflated size of the balloon may sometime vary from user to user, and also sometimes from time to time for the same user. Further, EP 2 683 424 discloses an electrically operated transanal irrigation system, where inflation of an inflatable balloon may be controlled by a pressure sensor. Still further, US 2014/0052063 discloses an irrigation system comprising a catheter with an inflatable balloon. A control system is provided for prevention of over-inflation of the balloon. To this end, the system monitors either the fluid pressure in the balloon as it is filled, or volume of fluid being provided to the balloon. Also, WO 2016/095929 discloses an electrically operated rectal irrigation system. It discloses the use of an electric pump for inflation of a balloon, and the pumping is controlled based on time duration or number of pump revolutions.

There is thus a need for improvements of the control of inflation of catheters having inflatable retention members in rectal irrigation systems, but also in other catheter systems having inflatable retention members, such as in urinary catheter systems, in endotracheal intubation systems, etc. In particular, there is a need for an irrigation device which can be used safely, easily and conveniently, and with improved controllability, for self-administration of the irrigation liquid, and which also preferably can be produced in a cost-efficient way.

SUMMARY OF CERTAIN EMBODIMENTS

In view of the above mentioned need, a general object of the disclosed embodiments is to provide methods and systems which inter alia alleviate the above-discussed problems of the prior art.

These and other objects can be achieved by a method and a system according to the appended claims.

According to a first aspect of the disclosed technology, there is provided a method for automated control of inflation of an inflatable retention member in a catheter by a controller, said method comprising:

providing a plurality of predetermined inflation levels;

providing, for each of said predetermined inflation levels, a pumping time threshold and a pressure level threshold;

continuously measuring the pressure in said inflatable retention member;

receiving input of a selected inflation level selected form said plurality of inflation levels; and operating an electric pump to inflate said inflatable retention member;

wherein said operating of the electric pump is continued until one of the pumping time threshold and pressure level threshold of said selected inflation level has been reached.

"Pumping time" corresponds to the total time during which a pump has been operative, regardless of whether the pumping has occurred continuously or with one or several interruptions. Thus, "pumping time" is the time since pumping started, but excluding the times during which the pump has been idle.

"Continuous measuring" corresponds to a measurement which is continuous over a certain period of time, such as during the entire inflation step, during the entire time the pump is active, during the entire irrigation process, at all times, or the like.

Catheters with inflatable retention members, such as an inflatable balloon, are used in many medical procedures where there is a need to retain the catheter in an inserted position during use. For example, such catheters are commonly used for catheters intended for insertion into the rectum, so-called rectal catheters, for example for use in anal irrigation systems, and for indwelling urinary catheters, for draining of urine from the urethra.

An appropriate inflation level should be such that catheter remains in place during use, but should also be such that it does not cause unnecessary discomfort and harm to the user, and in particular the inflatable retention member should not be overinflated to such an extent that there is a risk of burst or explosion of the inflatable retention member.

The appropriate inflation level of the inflatable retention member is difficult to determine beforehand, since it depends on the type of use and the size and type of catheter. It is also dependent on the preferences of the user; some users want the inflatable retention member to be quite large when inflated, whereas other users are more sensitive, and feel discomfort already at relatively small inflated sizes. Further, this may also vary over time for one and the same user, depending e.g. on the condition of the colon, the general condition of the user, etc.

The disclosed embodiments allow the user or operator to select among several predetermined inflation levels. Hereby, different inflation levels may be selected in dependence on the particular user, the type and size of catheter being used, the present condition of the user, etc.

It has been found by the present inventors that even pumping time, corresponding to the volume being provided to the inflatable retention member, and the pressure level of the inflatable retention member are both relevant to determine the inflation level of the inflatable retention member, and both are correlated to the size of the inflatable retention member. However, it has also been found that neither of these parameters are by themselves are sufficient to determine an adequate inflation level. It has been found that the correspondence between size of the inflatable retention member and pumping time and pressure level are complex relationships, depending on catheter size, conditions in the user, such as in the urethra or rectum, etc. For example, muscle contraction in the rectum may result in high pressure in the retention member even at fairly small volumes. Similarly, in the trachea there are periods of high pressure during the respiratory cycle. Also, at small inflated sizes, the pressure variation is very low, making it very difficult to adequately control the inflation size solely based on the pressure level. By not relying solely on pumping time, the sensitivity for pump tolerances and the like becomes less, and calibration of the pumps and other operations may hereby be performed less frequently, without affecting the overall performance of the system.

However, by controlling the inflation in relation to both pumping time and pressure level, a very efficient and predictable size can be obtained at the various inflation levels, and at the same time, it can be ensured that there is no over inflation, ensuring that there is no risk of burst or explosion of the inflatable retention member.

To this end, each inflation level is associated with both a pumping time threshold and a pressure level threshold, and pumping to a desired, selected inflation level continues until either of these thresholds has been reached. Thus, in rare cases, the pumping may be stopped when both the threshold for the pumping time and the threshold for the pressure level have been reached, if this occurs simultaneously. However, in most cases, one of these thresholds will be reached first, thereby aborting the pumping when the other parameter is below the set threshold value.

The disclosed technology also makes it possible to control various catheter sizes with the same control unit and with the same control settings. This is of particular importance when there are catheters of various sizes that can be connected to the catheter system, since the manufacturer may then have difficulties in knowing which catheter the user will use at each occasion.

The double threshold control also ensures proper inflation even during contextual variations, such as variations in the counter pressure of the colon.

The inflation method of the disclosed embodiments is also relatively simple to realize, install and operate, thereby making the resulting method/system cost-efficient and user friendly.

An electric pump is of great advantage, in particular in irrigation systems, since it can be operated very easily, which is particularly advantageous for users with reduced dexterity. If the user lacks strength in their hands it may be easier for them to operate an electric pump rather than squeezing e.g. a foil-pump. The electric pump can also easily be adjusted and customized for different types of use, for different types of users, etc.

Preferably, the plurality of predetermined inflation levels can include at least 3 different inflation levels, and preferably at least 5 different inflation levels. The inflation levels can, in the case of three levels, e.g. be denominated 1, 2 and 3; A, B and C; S, M and L; or the like, or be illustrated by schematic representations of balloons in three different sizes. The user may select a desired inflation level in various ways, such as by using a button or key dedicated for the specific inflation level, by selecting a level in a menu or the like, by using + and − buttons to increase and decrease the present level, etc.

The plurality of predetermined inflation levels preferably ranges from a lowest inflation level to a highest inflation level. The pumping time threshold or the pressure level threshold may in some embodiments be the same for two consecutive inflation levels. However, preferably the pumping time threshold and the pressure level threshold both increase incrementally between each predetermined inflation level from the lowest inflation level to the highest inflation level. Thus, the combination of thresholds for the pressure level and pumping time is unique for each predetermined inflation level, and preferably, both thresholds for each level are unique.

The pumping time thresholds are preferably all within the range 0.1-60 seconds, and preferably within the range 0.5-30 seconds, and most preferably within the range 1-15 seconds. For example, the predetermined pumping times may be set to 1 s, 5 s and 10 s, when three predetermined pumping levels are used, or 1 s, 3 s, 5 s, 7 s and 10 s, when five predetermined pumping levels are used. The exact pumping time thresholds may be set based on the type of catheters used, the pumping capacity of the pump, etc. However, advantageously, due to the precise control provided by the methods and systems of the disclosed embodiments, there is no longer any need for setting different levels for different catheter sizes. Instead, the same threshold levels may be used regardless of catheter size, which makes use of the method/system much easier for the user, and limits the risk of inadvertent errors in the setup.

The pressure level thresholds are all preferably within the range 1-500 mbar, and preferably within the range 2-300 mbar. As used herein, mbar represents the gauge pressure, or so-called bar(g) or simply barg, i.e. the pressure in bars above ambient or atmospheric pressure.

The continuous measuring of the pressure in the inflatable retention member is preferably made by a pressure sensor arranged directly in the inflatable retention member, or in a conduit being in direct communication with the inflatable retention member. Thus, in one embodiment, the pressure sensor may be arranged inside the inflatable retention member, and e.g. be connected to the control unit via an electric wire or the like. In another embodiment, the pressure sensor is arranged at a distance from the inflatable retention member, but in the lumen leading to the inflatable retention member, or in a conduit connected to this lumen, but ahead of any obstacles that would affect the pressure, such as one-way valves and the like. It is also possible to use more than one pressure sensor, and to arrange the pressure sensors at different locations.

The method and system in some embodiments provide control during inflation of the inflatable retention member, when the catheter has been arranged in the intended position, and ensures that the inflatable retention member is inflated to the desired size and volume, by monitoring both the pumping time and the pressure in the balloon. However, during this inflation process, it may also be possible to allow for temporary deflation, e.g. when a slight repositioning of the catheter is necessary or the like. During such deflation, the deflation time may be monitored, and translated into a corresponding negative pumping time in accordance with a predetermined relationship. Thus, the measured overall pumping time may consequently be reduced during deflation, with a time corresponding to the time it will take for the pump to re-inflate the balloon to the same size it had prior to deflation. If for example, in one it has been determined that during deflation, the flow through the release valve is C times the flow obtained during pumping, and an inflation process involves one or several of inflation, Ti, and one or several periods of deflation Td, the total pumping time, Ttot, to be compared with the pumping time threshold may be obtained as:

$$Ttot=Ti-C*Td$$

Further, the disclosed embodiments are particularly useful for controlling the inflation of the inflatable retention member. However, after the initial inflation, the control system may continue to monitor both the total pumping time and the pressure level in the balloon, thereby continuously adjusting the inflation level of the balloon during use. For example, the overall pressure in the colon during anal irrigation may vary during the irrigation process, thereby also affecting the pressure inside the inflatable retention member.

Thus, according to one embodiment, the method/system further comprises continuing to monitor the pressure level and the pumping time during use of the catheter, and to continue inflation of the inflatable retention member when both the pressure is below the pressure level threshold and the pumping time is below the pumping time threshold, and to deflate the inflatable retention member when either of the thresholds are exceeded or exceeded by a predetermined value. Hereby, the pumping time is preferably reduced during deflation in the way discussed above, but other ways of reducing the pumping time during deflation can also be contemplated. Thus, if e.g. the pressure drops in the balloon during use, and the total pumping time has not yet been reached, inflation will be resumed until either of the thresholds has again been reached. Similarly, if the pressure is increased in the balloon during use, thereby exceeding the pressure level threshold, or exceeds the threshold with a certain value, such as exceeding the threshold with X % or with Y mbar, the release valve may be operated to deflate the balloon until the pressure level is again at the threshold level. At the same time, the total pumping time is reduced with a corresponding time value.

According to another aspect of the disclosed embodiments, there is provided a catheter system comprising:

a catheter having an inflatable retention member;

an electric pump for pumping a fluid for inflation of said inflatable retention member;

a pressure sensor continuously sensing the pressure in the inflatable retention member;

a controller for automated control of said electric pump, the controller comprising a memory storing a set of inflation levels, each level being correlated to a pressure level threshold and pumping time threshold; and a user interface arranged to receive input of a selected inflation level selected form a plurality of predetermined inflation levels;

wherein the controller is arranged to operate the electric pump until one of the pumping time threshold and pressure level threshold of said selected inflation level has been reached.

With this aspect, similar advantages as discussed above in relation to the first aspect are obtained.

The controller is preferably arranged to obtain input from the pressure sensor continuously, and to control the electric pump in real-time.

The plurality of predetermined inflation levels preferably ranges from a lowest inflation level to a highest inflation level, and wherein the pumping time threshold and the pressure level threshold both increase incrementally between each predetermined inflation level from the lowest inflation level to the highest inflation level.

The irrigation system further preferably comprises a control unit with a housing, said housing enclosing said controller, said electric pump, and said pressure sensor.

The control unit may further be provided with a display and said user interface to receive input of a selected inflation level.

Another aspect of the disclosed embodiments is directed to use of the catheter system as discussed above and in the following for rectal and/or stomal irrigation.

The method and system of the disclosed embodiments is particularly useful for use in rectal or anal irrigation system, as well as in stomal irrigation. However, the disclosed methods/systems are also useable in other catheter systems having inflatable retention members, such as in urinary catheter systems, in endotracheal intubation systems etc.

In rectal or anal irrigation, an irrigation liquid is introduced into the rectum and lower intestine of a patient in order to induce bowel movement. The need for such a procedure typically arises in patients suffering from certain physical ailments in which voluntary bowel control is impaired or when the bowel needs to be cleaned before e.g. a coloscopy or a surgical operation. To this end, irrigation systems may be used e.g. by people suffering from spinal cord injuries, spina bifida or multiple sclerosis. For such users, irrigation may improve quality of life by preventing constipation, reducing time spent for bowel emptying procedures, reducing fecal incontinence, and by increasing independency and quality of life in general.

The irrigation method/system of the disclosed embodiments is portable, of limited size and relatively simple to use and control, also for user's having reduced dexterity. This makes it very well suited for self-administration, i.e. when irrigation is performed outside medical attendance premises, such as in the patient's home, and is performed by the patient himself. Further, portability of the irrigation system is important to disabled persons who are not hospitalised or bed-ridden if they are to live as normal a life as possible. This is particularly important if they travel away from their home, for instance, to someone else's home or if they stay in a hotel. In this situation, they need to be able to deal with their bowel function easily.

Thus, the new irrigation system facilitates operation, in particular for users having reduced dexterity. The whole irrigation procedure hereby becomes easier, faster and easier to control, and at the same time the overall safety is increased, and in particular the risk of explosion of the inflatable retention member is prevented.

When used as an rectal or anal irrigation system, the catheter is a rectal catheter, and preferably the irrigation system further comprises:

a reservoir for an irrigating liquid;
tubing providing fluid communication between said reservoir and said catheter; and
an electrical pump for indirectly pumping irrigation liquid from the reservoir to the probe through said tubing, wherein said electrical pump is either the same as the electric pump for pumping a fluid for inflation of the inflatable retention member, or a second pump.

The tubing may include a first part connecting the control unit with the probe and a second part connecting the reservoir with the control unit, and in which each of said first and second parts comprises a gas conducting tube and an irrigating liquid conducting tube. Hereby, gas can be pumped from the electric pump in the control unit to the reservoir, irrigation liquid may be transferred from the reservoir to the irrigation probe, via the electrically operable valve, and a gas may be pumped from the control unit to the inflatable retention member of the probe.

The electric pump for pumping irrigation liquid is preferably arranged for indirect pumping of the irrigation liquid. Hereby, the pump pumps a different fluid, such as air, into the reservoir, thereby increasing the pressure in the reservoir, and as a consequence forcing irrigation liquid out from the reservoir, for discharge through the probe. For example, the electric pump may be arranged to pump a gas, and preferably air, into the reservoir to create a pressure in the reservoir to displace the irrigation liquid therefrom and feed it to the probe.

The tubing is preferably arranged so that the control unit is arranged at a distance from both the reservoir and the probe, and being connected to the reservoir and probe, respectively, through the tubing. This makes it possible to have the reservoir at a distance from the control unit, e.g. on the floor, and still provide a good working position for the user.

The control unit further preferably comprises control elements for operation of the irrigation system. Preferably, the control unit comprises control elements for pumping of irrigation liquid, and for inflation and deflation of the inflatable retention member. The control unit also comprises control elements operable to set the desired inflation level. However, alternatively, the desired inflation level may be set through a remote control or the like.

The control unit further preferably comprises a display. The display may be used to assist in and confirm the selection of the desired inflation level. Thus, the display may be used to show different available inflation levels for the selection, and may also be used to show the selected inflation level, once the selection has been made.

Further, the display may be used to display information to the user about the progress of the irrigation procedure, such as volume that has been pumped, present flow rate, time elapsed from the start of the procedure, or estimated time left, etc. Further, the display may be used to guide the user about what choices in terms of settings and the like that are needed, the present function of the control elements, etc.

Still further, the display may be a touch screen, useable also for inputting data into the system. For example, the control elements may be realized as areas on the touch screen. If the control unit is connected wirelessly to a remote control or other remote unit, the display on this device may be used to display information as well. Thus a display on a remote control or other remote unit may be used to replace the display on the control unit, or to complement a display on the control unit.

In a preferred embodiment, the control unit comprises a valve, and preferably an electrically operable valve, for releasing fluid from the retention member for deflation, said valve being controllable by a control element, and preferably a control button.

Inflation of the inflatable retention member may be performed in various ways. In one embodiment, inflation is started by the user, e.g. by pushing a control element, such as a button or key, whereupon the inflation automatically proceeds until the selected inflation level has been reached, i.e. the threshold for pumping time and/or pressure level has been reached. Alternatively, inflation only occurs when a dedicated control element, such as a button or key is depressed, thereby functioning as a dead man's handle, thereby immediately returning to a deactivated state, in which the electrical pump is controlled not to pump, when manual operation of the control element is aborted. Thus, the inflation pumping can at any time be aborted by the user or operator. However, when, at any time, pumping is resumed, the automated pumping continues from the state where it was aborted. Thus, the controller continues counting the time, adding to the time during which pumping has so far occurred, and continues to receive information on the pressure in the inflatable retention member. Thus, the controller assures that pumping will be stopped as soon as the aggregated pumping time exceeds the pumping time threshold for the selected inflation level, the pressure sensed by the pressure sensor exceeds the pressure level threshold, or the control element for pumping is released. If the pumping has been aborted due to release of the control element, the pumping will be resumed and the process be continued as before when the control element is once again activated.

Similarly, the control element(s) for pumping the irrigation liquid may be arranged as separate control element(s), and may also be assigned to a dead man's functionality.

By means of this dead man's handle functionality it is ensured that pumping is immediately aborted when the control element is released. This means that the pumping action is stopped immediately when the control element is released, regardless of whether this release is intentional or by accident. For example, the pumping will stop immediately if the control element is accidentally dropped. Further, stopping by releasing is a very intuitive and quick operation method, which is both ergonomically favourable and fast. Thus, at least one, and preferably both, of the control element(s) that control the pumping of the irrigation liquid and the control element(s) for pumping fluid for inflation of the inflatable member preferably functions as a dead man's handle, thereby immediately returning to a deactivated state, in which the electrical pump is controlled not to pump, when manual operation of the control element is aborted.

The control elements are operable by applying a predetermined condition to bring the control element into the activated state, and preferably at least one of depression, twisting, rotating, pulling and pushing. If a control button is used, the predetermined condition is preferably depression, so that the control button is activated by depressing it, and deactivated by releasing it. However, alternative types of control elements, such as rotatable knobs, switching levers and the like may also be used. An automatic return to the deactivated state when the predetermined condition ceases can e.g. be obtained by a spring, an elastic element, or the like, operable to provide a counterforce to the force applied by the manual operation. The control elements, such as control buttons, may be arranged on the surface of the housing. The control elements may e.g. be realized as areas on a touch screen.

The control unit preferably comprises at least two control elements, such as control buttons, and preferably at least three control elements. Two, or preferably three, control elements enable a very easy manipulation of the control unit, and at the same time provides numerous input alternatives. It is further preferred that at least one of the control element(s) is a multi-purpose control element having different functions in different operation states. Hereby, the control elements can e.g. be assigned to control different functions during initiation/set-up and during operative use.

One or several control elements may also be arranged separated from the control unit, and may e.g. be connected with the control unit by means of wire, and thereby be physically connected to the electric pump etc. Alternatively, the control elements may be arranged on a remote control, which is wirelessly connected to the rest of the irrigation system. The remote control can e.g. be at least one of: a smart phone, a tablet computer and a laptop computer. It is also possible to combine a control unit with integrated control elements and a remote control, whereby the user may choose whether to use the integrated control unit or the remote control, or both, for controlling the irrigation process.

By the use of a remote control, the control unit may e.g. be placed on the floor, or in any other resting position, and instead be operated through the remote control during irrigation. This facilitates handling of the irrigation system, and affords the user an increased freedom in terms of how to use the system. The remote control may be a dedicated remote control, specifically arranged to control the irrigation system. However, the remote control may also be a common wireless device, capable of transmitting wireless control signals to a receiver in the control unit. In one preferred embodiment, the remote control is a mobile telephone, and preferably a smart phone. Additionally or alternatively, the remote control may be a laptop computer or a tablet computer. Hereby, a special application may be downloaded to the smart phone/laptop/tablet computer, providing a suitable interface for the device, and enabling it to send appropriate control signals to the control unit.

The wireless communication between the control unit and a remote control or a remote unit may be obtained in many ways, as is per se well known in the art, such as by infrared light (IR), ultrasonic communication, radio frequency (RF) communication, such as Bluetooth, etc.

The control unit is further preferably provided with a battery for driving the electric pump(s).

The control unit may further comprise a preferably waterproof housing enclosing at least said battery. Further, the electrical system of the irrigation system may be galvanically isolated from the exterior of the irrigation system, and wherein the battery is chargeable through inductive charging. A waterproof housing and galvanic separation between the electric system and the surrounding environment makes the system very robust. It can hereby withstand for example spilling of water, or even accidental submersion of the control unit etc. in water. Since an irrigation system is typically used in close relation to water and other liquids, this is often an advantage. This also makes it possible to use the system, or components of the system, for longer time, which provides a better overall cost-efficiency. However, for many types of applications, a waterproof housing and/or a galvanically isolated electric system may not be necessary.

However, it is also feasible to charge the battery by conventional, wired charging. It is also feasible to power the irrigation system during use from an external source, such as being plugged in to the ordinary power supply system. In this case, the battery may even be omitted.

The controller is preferably programmable. For example, the controller may be programmable to set the predetermined inflation levels, and to select the desired inflation level. Further, the controller may be programmable to set a maximum filling level of the inflatable retention member. The maximum filling level may be a fixed level, defined by the producer, a physician or the like. This increases the safety of the irrigation system, since inadvertent overfilling of the inflatable retention member can hereby be even further avoided.

Further, the controller may be programmable to set the flow rate and/or the total irrigation liquid volume to be discharged. The controller may be pre-programmed with a number of programmes or it may be programmed via the control element(s) or through an external remote control or the like. The controller may be programmable so as to automatically carry out a predefined program. A user that frequently uses anal irrigation may experience a preferred way of carrying out the irrigation process. Then it is of advantage to be able to programme this way into the controller, so that the irrigation process is done the most preferred way every time. Furthermore, caregivers may have a certain experience concerning the optimum process, which they can programme into the controller. Thereby errors will be reduced.

The method/system discussed above is very reliable, and ensures that the inflatable retention member is automatically inflated to the desired size at all times, and ensuring that no over inflation occurs. However, as an extra safety measure, the irrigation system may further comprise a safety element, preferably realized in hardware, being separate from the controller and being connected to the pressure sensor, whereby the safety element is arranged to stop the pump when the sensed pressure in the inflatable retention member reaches or exceeds a predetermined maximum safety value. Hereby, it is ensured that pumping will automatically stop even in e.g. the unlikely event of an error in the controller. The safety element is preferably realized in hardware, and functions as a switch or breaker that is automatically activated to turn off the pump if the pressure reaches or exceeds a predetermined maximum value.

Preferably, all components of the irrigation system are individually exchangeable, so that e.g. the probe/catheter can be exchanged frequently, and typically be used only once, whereas other parts of the system, such as the control unit, the electrical system and the irrigation liquid reservoir can be used for months or even years.

The irrigation system of the disclosed embodiments comprises relatively few and uncomplicated components, and which may be reused for a long time, which makes the irrigation system relatively easy and cost-efficient to produce. Further, the irrigation system lends itself well for automated or semi-automated manufacturing.

The irrigation system of the disclosed embodiments is also highly suitable for self-administration of the irrigation liquid. The control elements on the control unit also make it easy to access the pump(s) with one hand only, and to switch between different pumping modes etc. Typically, with this arrangement, it is e.g. possible to operate the irrigation system with one finger, e.g. the thumb. This provides a very convenient and precise controllability of the irrigation system.

The inflatable retention member is preferably inflated with a gas, and most preferably air. However, the inflatable retention member may also be inflated with a liquid, such as water. Thus, the pump may alternatively be arranged to pump any other such inflation fluids, either directly or indirectly, to the inflatable retention member.

These and other aspects of the disclosed embodiments will be apparent from and elucidated with reference to the embodiments described hereinafter.

BRIEF DESCRIPTION OF THE DRAWINGS

For exemplifying purposes, the disclosed embodiment will be described in closer detail in the following with reference to embodiments thereof illustrated in the attached drawings, wherein.

DETAILED DESCRIPTION OF PREFERRED EMBODIMENTS

Figure 1:
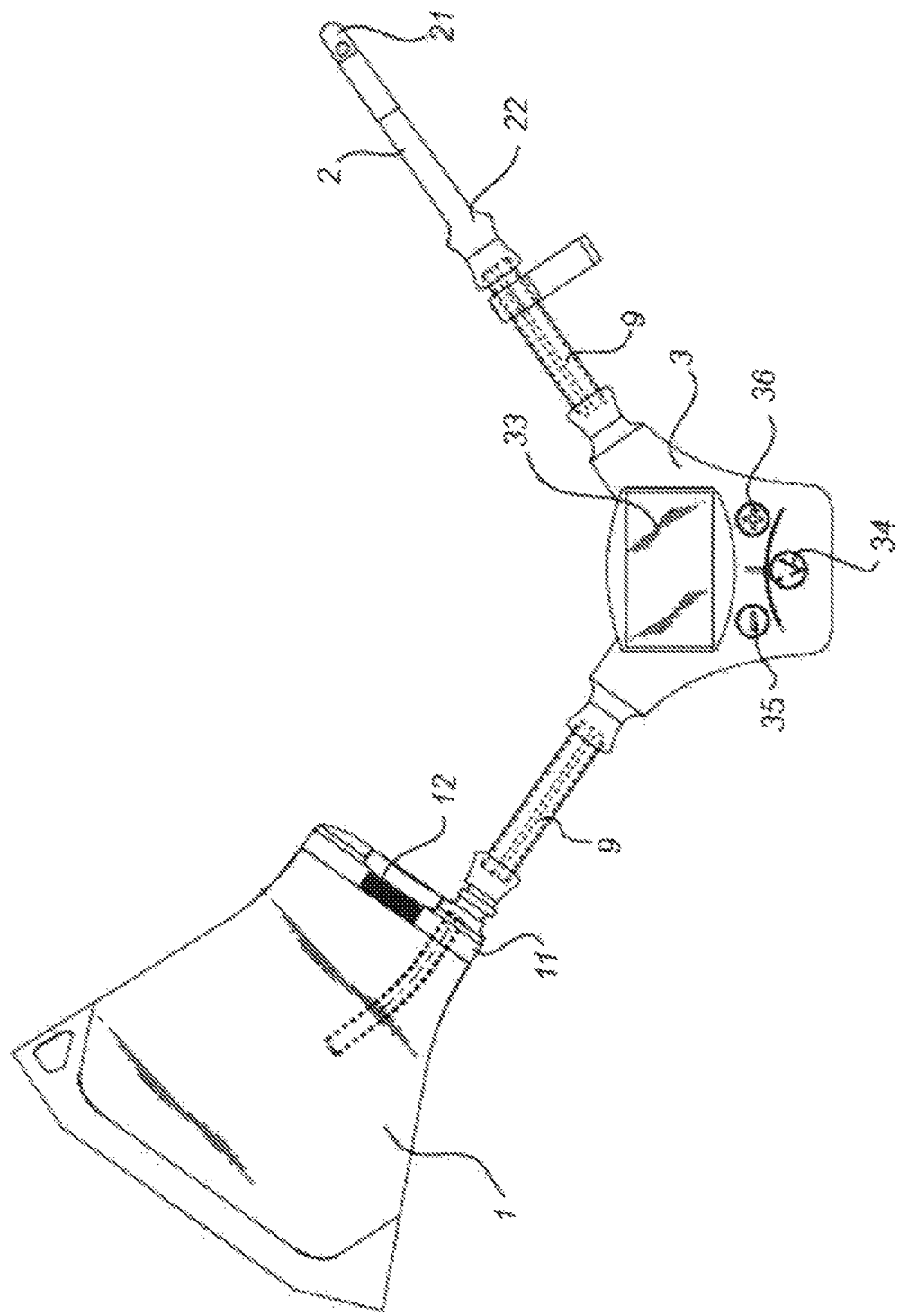
FIG. 1 is a schematic overview of an irrigation system according to an example embodiment.

The disclosed embodiments will now be described more fully hereinafter with reference to the accompanying drawings, in which currently preferred embodiments are shown. This disclosed embodiments may, however, be embodied in many different forms and should not be construed as limited to the embodiments set forth herein; rather, these embodiments are provided for thoroughness and completeness, and fully convey the scope of the invention to the skilled addressee. Like reference characters refer to like elements throughout. Further, in the following, an irrigation system, particularly useful for rectal irrigation, will be discussed. However, it is to be acknowledged by the skilled reader that the same control system and control method may also be used for other types of irrigation systems, as well as for other types of catheter systems and the like.

FIG. 1 discloses an irrigation system according to an exemplary embodiment, comprising a reservoir 1 for an irrigating liquid, a probe or catheter 2 for arrangement in a user, and a control unit 3. Tubing 9 is arranged to connect the reservoir 1 with the control unit 3 and the control unit 3 with the catheter 2.

The reservoir may be realized in various ways. For example, the reservoir may be formed by a rigid, semi-rigid or flexible material. In case a semi-rigid or flexible material is used, the reservoir may be collapsible or foldable, to make the irrigation system more compact prior to use. The reservoir is provided with an opening, closed by a lid 11, for filling of the reservoir. Tubing connecting the reservoir to the rest of the irrigation system may be provided through the lid 11, or through other access points on the reservoir.

As one embodiment, the reservoir may be a collapsible reservoir of the type disclosed in US 2015/335529, said document hereby being incorporated in its entirety by reference.

In order to render the irrigation system as portable as possible, the container preferably has a capacity of less than 5 litres, more preferred less than 3 litres and most preferred less than 2 litres. If however the system is to be used for repeated irrigation, a larger capacity container may be necessary.

The reservoir may comprise an overpressure release valve, to release pressure over a predetermined maximum pressure to be allowed. Further, the reservoir preferably comprises a filter 12, such as a hydrophobic filter, which is impermeable to the irrigation liquid, but which allows air to enter the reservoir but not escape the reservoir. Such a filter ensures that the reservoir maintains its shape when irrigation liquid is being pumped out from the reservoir. This is of advantage, since it makes the reservoir more stable. It also makes it possible to use less costly materials and less rigid containers when producing the reservoir, thereby making the production more cost-efficient. This ensures that the reservoir remains stable during irrigation. However, alternative means for obtaining this are also feasible. For example, the reservoir may simply be provided with an air inlet, possibly provided with a back-valve to prevent outflow of irrigation liquid, should the irrigation liquid reach the inlet.

The catheter 2 is here embodied as a rectal catheter. The probe is provided with an inflatable retention member 21, such as an inflatable balloon, for fixing the catheter in a body cavity. The inflatable balloon preferably protrudes as a toroidal shape when inflated, and is essentially flush against the wall of the catheter when deflated. The inflatable retention member may also be referred to as a balloon, and is arranged close to the insertable tip, but at some distance from the end. Between the tip and the balloon, an opening for dispensing liquid, such as irrigation liquid, or draining liquid from the body may be provided. The inflatable retention member may be made of any suitable material, such as PVC, latex, TPE or PU. However, other materials providing similar properties can likewise be used.

Further, the probe may be provided with a rearward enlarged part 22, providing an abutment to hinder too deep insertion. The probe is preferably provided with two lumens—one lumen for transfer of irrigation liquid through the probe, for discharge at the forward end, and one lumen for inflation and deflation of the balloon.

The probe may be of the type disclosed in WO 2014/154635, said document hereby being incorporated in its entirety by reference.

Tubing is arranged to connect the reservoir, control unit and probe together.

The irrigation liquid can be any liquid which is capable of irrigation the body cavity of interest. In order to stimulate bowel movements suitable irrigation liquids includes water, hypertonic aqueous salt solutions, solutions or suspensions of cathartic agents, such as bisacodyl or phenolphthalein, and mineral oil.

Figure 2:
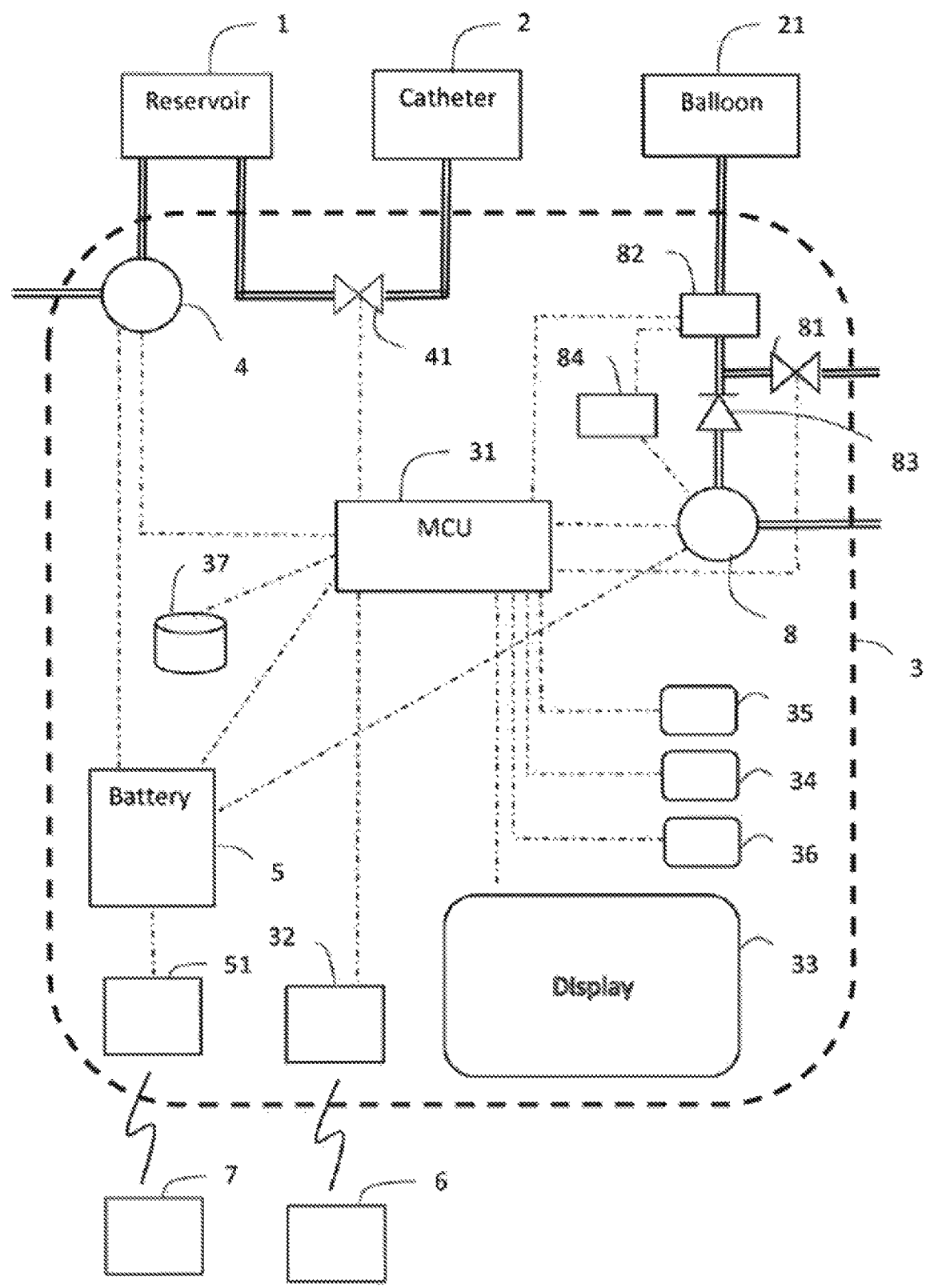
FIG. 2 is a schematic overview of a control unit for use in an irrigation system according to an example embodiment.

Referring now to FIG. 2, a first electric pump 4 for pumping irrigation liquid is here provided within the control unit 3, but may also be arranged outside the bounds and housing of the control unit. The pump is preferably part of the electrical system of the irrigation system, connecting the pump inter alia to a battery 5. The pump is preferably arranged to pump gas, e.g. air, into the reservoir 1 to create an overpressure, which forces irrigation liquid in the reservoir to be transferred to the probe 2. Such a system is e.g. disclosed in U.S. Pat. No. 7,914,505, said document hereby being incorporated in its entirety by reference.

The control unit is here realized as a unitary, hand-held unit. The control unit may comprise a display 33, and a user interface for providing input to the system, e.g. including one or several control elements. In the example of FIG. 2, three control elements 34, 35 and 36 are provided. The control elements are preferably realized as a depressible control buttons. The control unit is preferably waterproof. The control elements may thus be realized with thick pliable plastic or the like, designed to withstand many pushes. The further details and function of the control unit will be discussed in more detail in the following.

In this embodiment, another pump 8 is arranged to pump fluid into the inflatable retention member 21 of the catheter 2. This pump is also an electric pump. However, alternatively, either of the pumps 4 and 8 may be used as a single pump both for pumping of irrigation liquid and for inflation of the inflatable retention member. Thus, the second pump 8 (or the first pump 4) pumps air into the balloon 21 for inflation. The air is releasable through a valve 81, which may e.g. be controllable by one of the control elements, e.g. control element 34.

The control elements 35 and 36 may here be used to activate the pump(s) for inflation/deflation of the inflatable retention member, and/or for transferring of irrigation liquid through the probe for irrigation (control element 36), and for releasing overpressure and/or draining the system from remaining liquid (control element 35). Separate control elements may also be provided for irrigation and inflation, so that inflation and deflation of the retention member may take place independently of the irrigation, and e.g. simultaneously.

The electrical system of the irrigation system will now be discussed in more detail, with continued reference to FIG. 2. The electrical system is arranged within the housing of the control unit 3, and comprises an electric pump 4, as previously disclosed, connected to a battery 5 and a controller 31, such as a micro-processor. The controller 31 is further connected to the display 33, and to switches activated by means of the control elements 34-36.

The controller 31 may be a microprocessor, MCU, comprising one or several central processing units, CPU. However, the controller may also be realized in other ways, as is per se known in the art. Further, the controller 31 is preferably provided with one or several memories 37, either arranged integrated with the controller, or arranged as a separate component connected to the controller, as illustrated in FIG. 2. The memory may be a ROM memory, such as an EPROM or EEPROM, or a RAM memory, such as Flash memory. However, many other types of memories may also be used, as is per se well known in the art.

Further, the controller is optionally connected to a wireless transceiver 32, which is adapted to transmit and receive data from a remote unit 6. Hereby, the remote unit may provide control data to the controller 31, for remote control of the control unit. Additionally or alternatively, the controller may transmit data about the irrigation procedure to the remote unit. The remote unit 6 may e.g. be a remote control, a smart phone or the like.

The battery 5 is further connected to a charging circuit 51, adapted to receive inductive charging from a charging station 7, or to received direct charging from a connected electric conductor. All elements of the electrical system are connected by electrical wires. As discussed above, the electrical system may be galvanically isolated from the rest of the irrigation system and the environment.

The electric pump 4 is arranged to pump a fluid, and preferably a gas, such as air, through a conduit to the reservoir. Thereby, pressure increases in the reservoir to pump irrigation liquid through another conduit to the control unit. This conduit passes through an electrically operable valve 41 and optionally a flow sensor (not shown), and continues to the probe, for dispensing the irrigation liquid to the user. The valve 41 is connected to the controller 31, so that the controller may control the degree of openness of the valve. In case a flow sensor is provided, the input from the flow sensor may be used by the controller to regulate the valve 41.

The valve 41 may be an on/off valve, arranged only to assume a fully opened or fully closed state. However, the valve may also provide intermediate positions, and may e.g. be gradually controllable between these end states. Such an electrically operable valve can be realized in many ways, as is per se well-known in the art. For example, the electrically operable valve may be a clamping or pinch valve, providing a controllable clamping/pinching action on a tube leading between the electrical pump and the probe. For example, the valve may be of the type disclosed in US 2016/0114148 by the same applicant, said document hereby being incorporated in its entirety by reference.

Another pump 8 is arranged to pump air through another conduit leading from the control unit to the probe for inflation of the inflatable retention member 21. In the illustrated embodiment, different pumps are used for irrigation and inflation. However, as already discussed, a single pump may be used for both these purposes.

The pump 8 is controlled by the controller 31. Hereby, the controller may start and stop the pump, thereby starting and stopping the inflation, and may also possible control the operating speed of the pump. Preferably, the pump pumps air for inflation of the balloon. However, the balloon may also be inflated by other gases and liquids, such as water. Thus, the pump may alternatively be arranged to pump any other such fluids, either directly or indirectly, to the inflatable retention member.

The pump 8 pumps air (or other inflation fluids) through a one-way valve 83 and into the inflatable retention member 21. The one-way valve 83 prevents air from returning back from the balloon. Instead, a separate valve 81 is arranged for deflation. This valve 81 is also controlled by the controller 31. The one-way valve may be any type of check valve, as is per se known in the art, such as a ball, flap, duck bill, or umbrella valve.

A pressure sensor 82 is further arranged to measure the pressure in the balloon 21. The pressure sensor may be arranged inside the balloon, or in a conduit being in direct communication with the inflatable retention member. In the illustrative example, the pressure sensor is arranged in the control unit 3, and in the conduit between the inflatable retention member and the one-way valve 83.

The pressure sensor may any type of per se known pressure sensors. Preferably, the pressure sensor is a gauge pressure sensor, measuring the pressure relative to atmospheric pressure, and may e.g. be a piezoresistive sensor, such as a piezoresistive strain gauge, a capacitive sensor, an electromagnetic sensor, an optical sensor or the like. However, other types of pressure sensors may also be used.

The measurement output from the sensor 82 is forwarded to the controller 31, which may then control the operation of the pump 8 in accordance with this, as will be discussed in more detail in the following.

In addition, the pressure sensor 82 may also be connected to a safety element 84, which in turn is connected to the pump 8. The safety element is preferably realized in hardware, and functions as a switch or breaker that is automatically activated to turn off the pump 8 if the pressure reaches or exceeds a predetermined maximum value. Hereby, extra safety is provided, so that the pump will stop even in the unlikely event that the control of the controller 31 would fail.

Two or more predetermined inflation levels are accessible for the controller 31, and may e.g. be stored in the memory 37. The user may select a desired inflation level of said predetermined inflation levels, e.g. by operation of one or more of the control elements 34-36, or via the remote unit 6. For example, the predetermined inflation levels may be presented as symbols or in a text list on the display, and control elements 35 and 36 may be used to move around in the list, whereas control element 34 may be used to select one of the inflation levels. However, other methods for selecting an inflation level may also be used, as would be apparent for the skilled reader.

Figure 3:
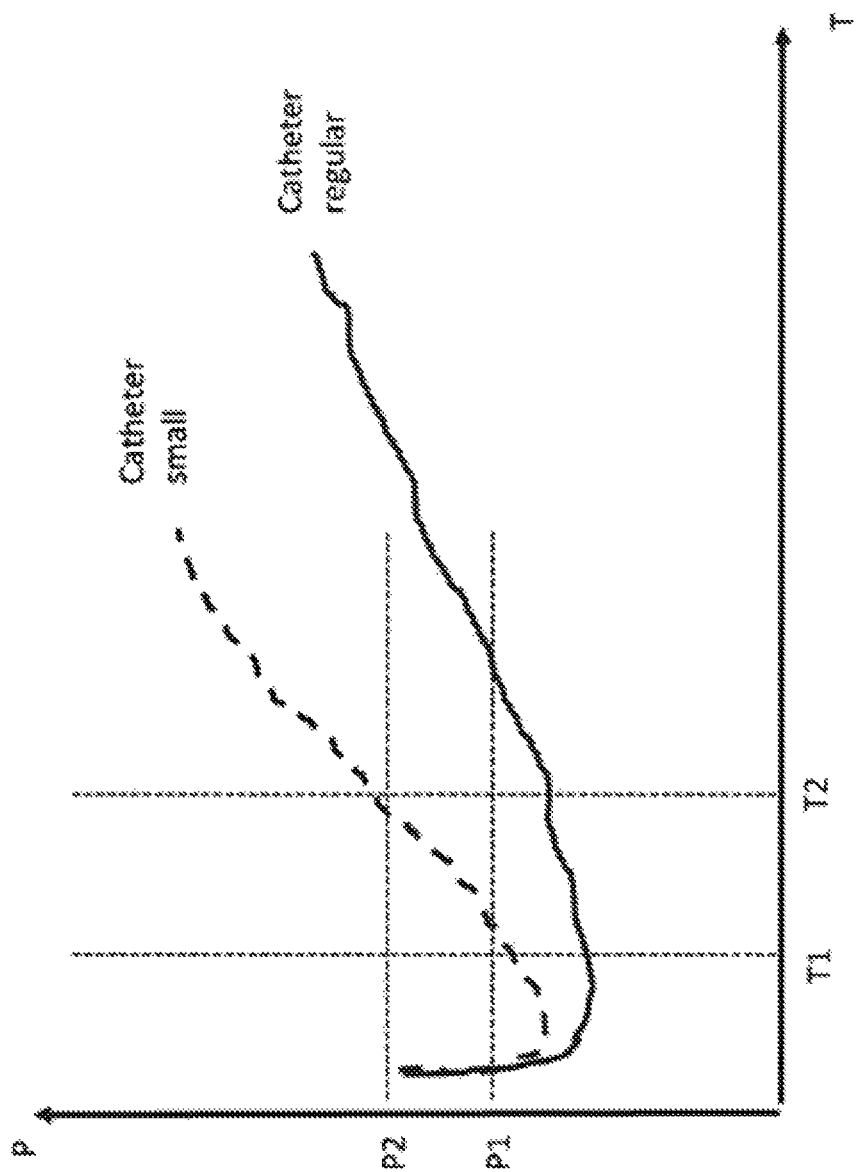
FIG. 3 is a diagram illustrating the pressure-time-curves for two exemplary rectal catheters of different sizes.

In the diagram illustrated in FIG. 3, a simple case with two predetermined inflation levels is shown. The first, smallest inflation level has a pumping time threshold of T1, e.g. 5 s, and a pressure level threshold of P1, e.g. 200 mbar. The second, larger inflation level has a pumping time threshold of T2, e.g. 10 s, and a pressure level threshold of P2, e.g. 300 mbar.

The pressure-time curves of two different catheters are shown—one relating to a regular size rectal catheter (solid line) and one relating to a smaller size rectal catheter (dashed line). As can be seen, the regular size catheter has a curve that rises slower than the small size catheter. If the user has selected the first predetermined inflation level, the regular size catheter will reach the pumping time threshold before the pressure level threshold has been reached, and will at that time turn off the pump. If the small size catheter is used, the pumping time threshold will also be reached first, thereby leading to a switch off of the pump, but just slightly prior to reaching the pressure level threshold. If the user has selected the second predetermined inflation level, the regular size catheter will again reach the pumping time threshold first, which leads to stopping of the pump before the pressure level threshold has been reached. However, for the small size catheter, the pressure level threshold will instead be reached first, which leads to stopping of the pump before the pumping time threshold has been reached.

However, this is just an example. Naturally, more than two inflation levels, such as three or five levels, may be used instead. Further, the pressure-time-curves may look different for other types and sizes of catheters.

Pumping for inflation of the balloon may commence upon activation of a switch or the like, such as depression of one of the control element 34-36. The pumping may then, once activated, proceed automatically until the controller 31 has determined that either of the thresholds has been reached. In this case, it suffices to count the time from when pumping started to determine the pumping time. However, the pumping may also occur only when the control element is maintained in an activated state. Hereby, the pumping may be stopped by deactivating the control element, and then restart as soon as it is again brought to an activated state. The pumping time will in this case be determined as the total pumping time during which pumping has actually occurred, disregarding the times during which the pump has been idle. However, upon reaching either of the thresholds, the pumping will immediately be aborted by the controller 31 in the same way as in the previous embodiment.

Performing pumping only when a control element is in an activated state provides a dead man's handle functionality. Thus, the control element is brought into the activated state by continuous application of a predetermined condition thereto, and is immediately brought to the deactivated state when the predetermined condition ceases to be applied, thereby aborting pumping. Such dead man's handle functionality may be used for pumping of the irrigation liquid, for inflation of the balloon, or both. The automatic return to the deactivated state when the predetermined condition ceases can e.g. be obtained by a spring, an elastic element, or the like, operable to provide a counterforce to the force applied by the manual operation.

Figure 4:
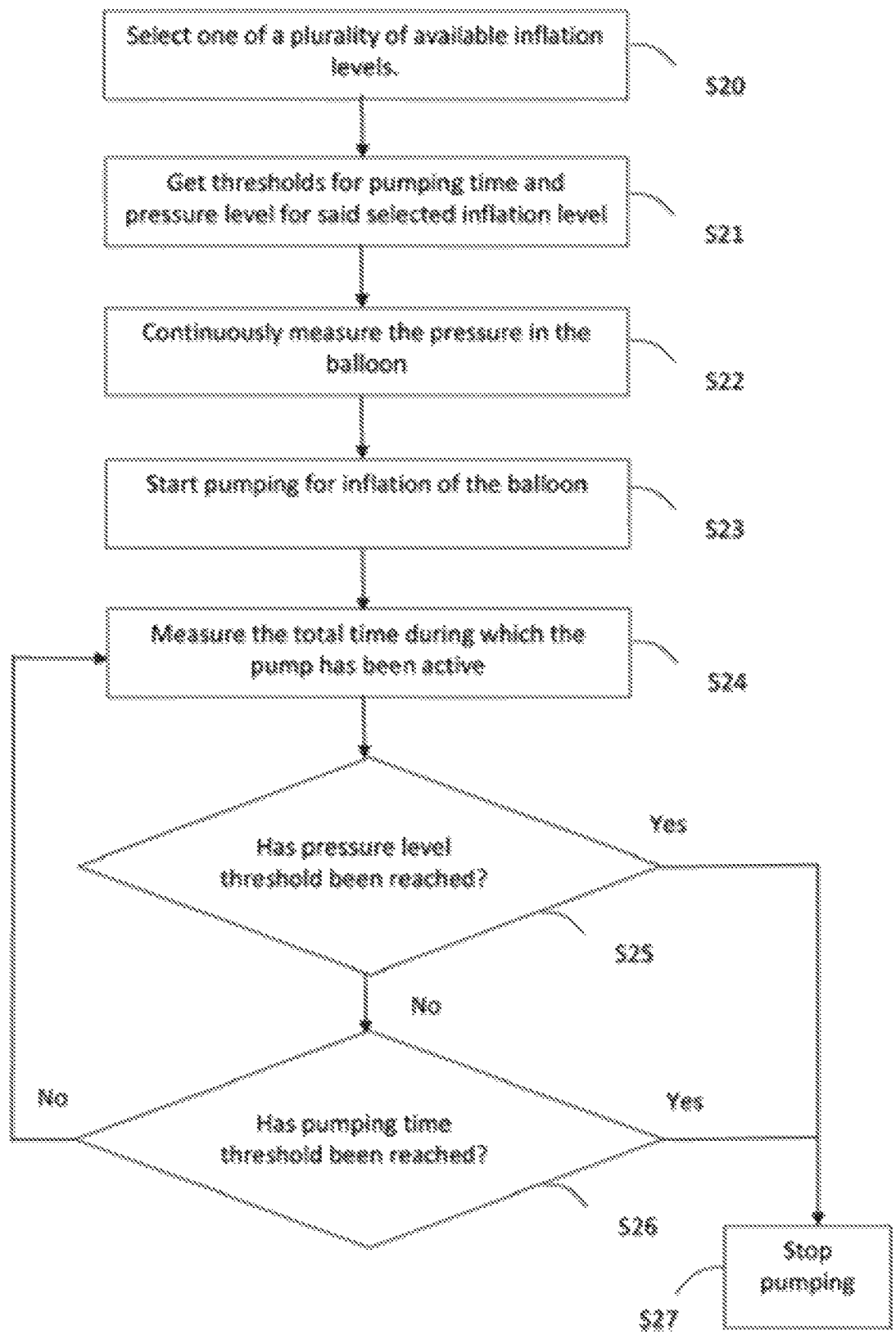
FIG. 4 is a schematic flow chart illustrating a method for controlling inflation of the inflatable retention member in accordance with one embodiment of the present invention.

In FIG. 4, a schematic method for controlling the inflation of the inflatable retention member with the controller is illustrated. In a first step, S20, the user selects one of the available, predetermined inflation levels, and the choice is received by the controller through the user interface. In a second step, S21, the pumping time threshold and the pressure level threshold associated with the selected inflation level are retrieved from the memory. The pressure level in the balloon is then continuously measured, step S22. Pumping is then initiated, step S23, again by receiving input from the user interface. The controller then keeps track of the total pumping time during which the pump has been active, disregarding any times during which the pump has been idle, step S24. It is then determined, in step S25, whether the first threshold, e.g. the pumping time threshold, has been reached. If yes, the pumping is immediately brought to a halt, step S27. If not, it is then determined whether the second threshold, e.g. the pressure level threshold, has been reached. If yes, the pumping is immediately brought to a halt, step S27. If neither of the thresholds has been reached, the process returns to step S24 in an iterative process.

The number of control elements, and the configuration of the control unit, may naturally be made differently. It is also possible to use other types of control units, and to implement e.g. the flow rate control in relation to other types and configurations of control elements. One such alternative embodiment of a control unit is illustrated in FIG. 5.

Figure 5:
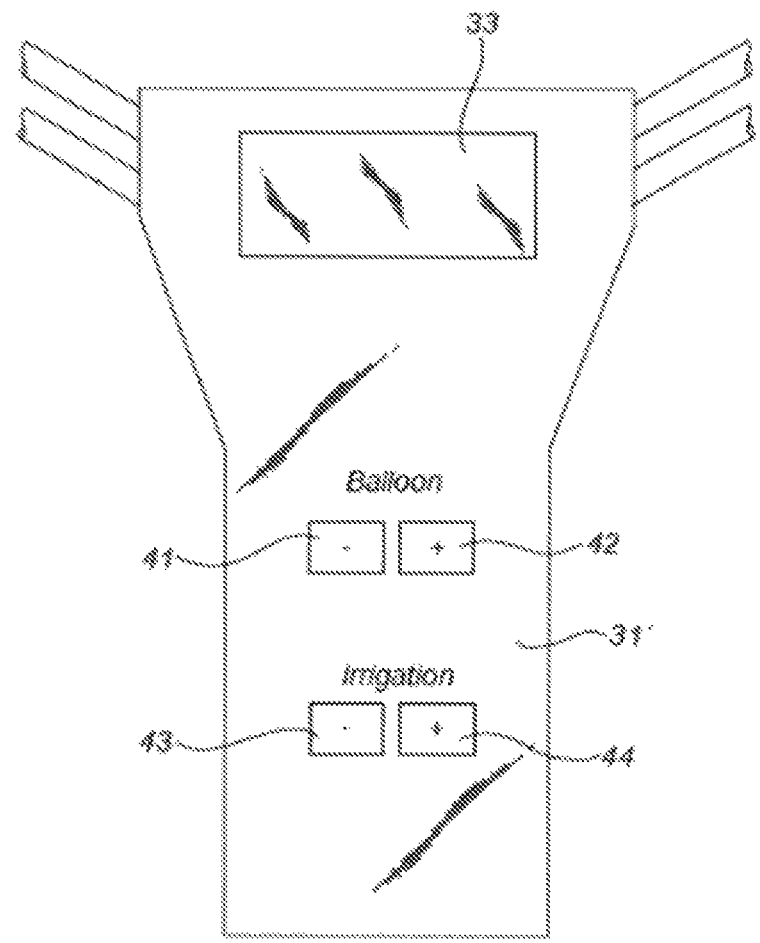
FIG. 5 is a schematic overview of an alternative embodiment of a control unit useable in irrigation systems.

In the control unit of FIG. 5, the control unit 31' is provided with separate control elements, here in the form of control buttons, for irrigation and for inflation/deflation of the balloon on the probe, respectively.

It is possible to use the same control element for both inflation and deflation of the probe, e.g. by using a rocker lever or the like, having three states—inflation, deflation and non-operative. The non-operative state should be default, and as discussed above, the non-operative state should preferably automatically be resumed as soon as the control element is released. However, preferably separate control elements, such as buttons are used for inflation and deflation, respectively. In the illustrative example, a first button 41 is used for deflation of the balloon, and a second button 42 is used for inflation of the balloon. Again, the buttons may be operative only when depressed, and release of the buttons may immediately stop the inflation/deflation processes.

Similarly, the irrigation is controlled by one or several control elements. For irrigation, only one operation is normally required, viz. to activate the pump to provide irrigation fluid to be transferred to the user through the probe. This may be controlled by a control button 44, as in the illustrative example. Irrigation will, as discussed above, preferably immediately be aborted once the button 44 is released. A further control button 43 may be provided for reverse operation, e.g. to empty the tubes and the probe from irrigation fluid once irrigation has been completed, and/or to release overpressure from the irrigation liquid reservoir. This control element is preferably also provided with a dead man's handle functionality. Alternatively, a single control element with several operation states, such as a rocker lever, may be used here as well.

The arrangement of separate control elements for controlling the balloon on the one hand, and the irrigation on the other, presents several advantages. For example, the control unit becomes simpler and less costly to produce. Further, the operation becomes more transparent and controllable for the user.

It is possible to make the control elements for the balloon and the irrigation, respectively, to be operable only one at a time, i.e. to lock the other control elements when one is used. However, in one embodiment the control elements for the balloon and irrigation, respectively, are operable simultaneously. This makes it possible for the user to adjust the balloon filling, by inflation or deflation, during irrigation.

Figure 6:
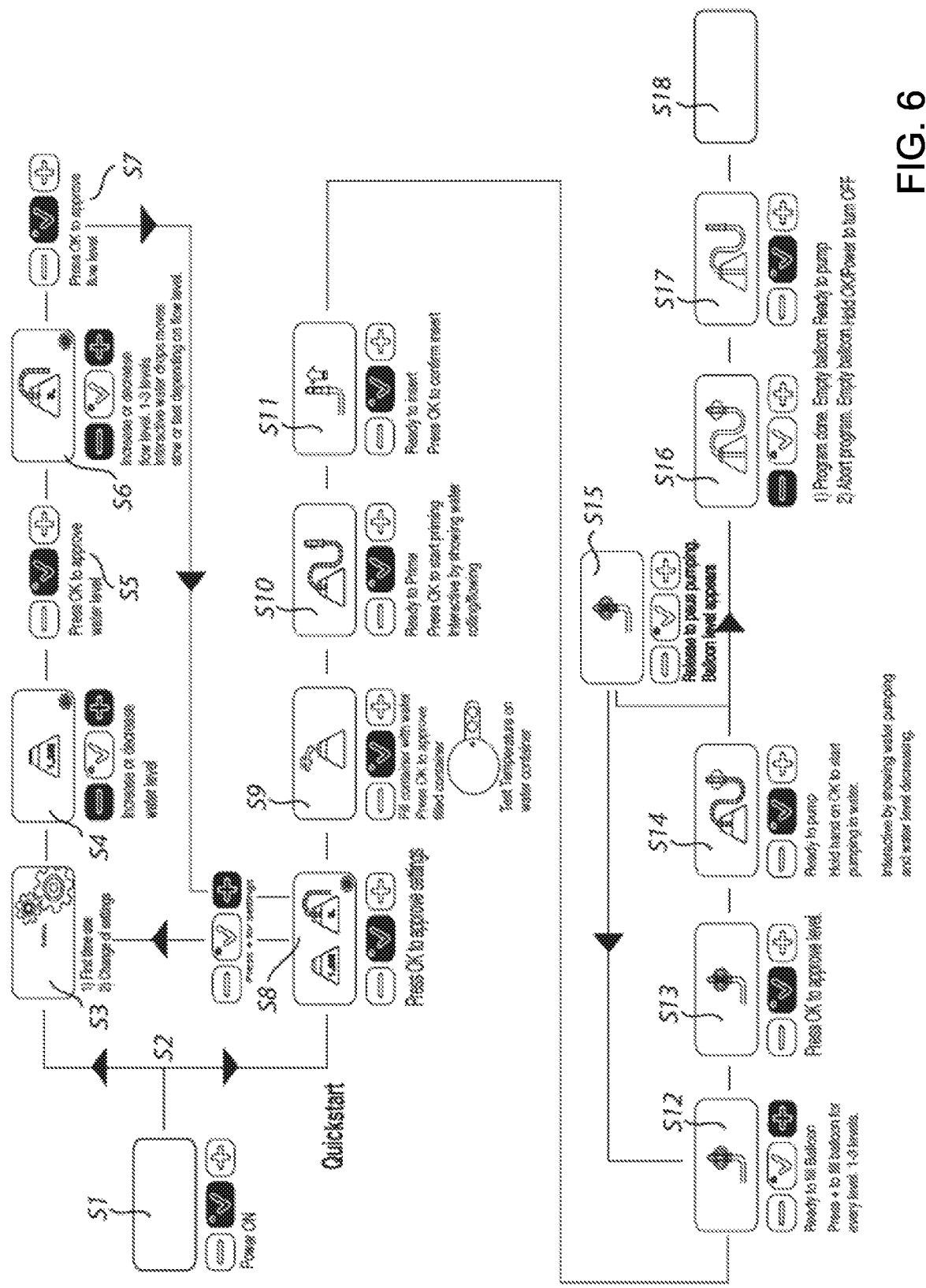
FIG. 6 is a schematic overview of the steps of an irrigation procedure using an irrigation system according to an example embodiment.

According to the disclosed embodiments, anal irrigation can be carried out by a sequence of steps, which will now be discussed with reference to the schematic illustration of possible display showings, as illustrated in FIG. 6.

Here, three control buttons are used: one marked as "−", indicating a decrease, one marked "+", indicating an increase, and one marked "√", indicating a confirmation, OK. These buttons will be referred to in the following as "decrease", "increase" and "confirm", respectively.

In a first step S1, the control unit is activated, and a choice is made, S2, whether to enter an initiation scheme, or to quick-start the irrigation procedure. If this is the first time the irrigation system is used by the user, the initiation scheme is preferably required, whereas for a restart or a reuse of the irrigation system the quick-start path may be chosen. However, the initiation scheme may be used even after the first time, to alter the settings and the like.

In the initiation scheme, a display is first shown, S3, that a parameter setting mode is entered. In a following step, S4, the inflation level is determined, and additionally the volume of irrigation liquid to be used for the irrigation may be determined. The desired inflation level and optional volume is/are set with the increase and decrease buttons. In a following step, S5, the set volume is accepted by pressing the confirm button. However, this step may also be omitted, in which case the process proceeds immediately to the next step. In a following step, S6, the desired flow rate may be determined. Again this is done with increase and decrease. The flow rate is preferably selectable among a predetermined number of pre-selected fluid rates. For example, three, four, five or more different flow rate levels may be provided. In a subsequent step, S7, the selected level is confirmed.

The settings for the user are preferably stored, and are reused in the next irrigation. The parameter settings may e.g. comprise one or several of: total irrigation liquid volume, flow rate for the irrigation liquid and fluid volume for inflating the inflatable retention member. It is also possible to store several parameter settings, or even storing of the parameter settings for every irrigation process being conducted, and to select and retrieve any of these stored parameter settings for reuse.

The user is then asked whether the determined settings are accepted in step S8. Pressing of confirm at this stage brings the user forward to the next stage, whereas a negative confirmation, e.g. by pressing increase, brings the user back to the setting stage, step S3. However, step S8 may also be omitted, and the process may immediately go from step S1 to step S9. In this case, the parameter setting process may be reached by activating a separate "setting" button, or by any other means useable to change mode.

Having completed the initiation, the user is requested, in step S9, to fill up the reservoir with liquid, such as water. When this is done, confirm is pressed to confirm completion of this step. However, confirmation is optional, and may be omitted. In this case, the process will proceed to the next step immediately, without requesting confirmation. Optionally, a temperature check of the filled liquid can be done at this stage, and an alarm may be provided to the user if the temperature is too high or too low.

In a following step, S10, the user is asked to confirm that priming of the system should be made. Priming may e.g. comprise pumping of irrigation to fill the tubing with liquid, etc. At this stage, the probe may remain in its package. If the probe is provided with a hydrophilic coating, irrigation liquid may also be pumped to ensure that the hydrophilic coating is properly wetted and activated. However, the confirmation may again be omitted, in which case the priming step is performed without request for a confirmation. Further, for some applications the entire priming step may be omitted.

When priming is completed, the user is asked, in step S11, to insert the probe in the operational position. When this has been done, this is confirmed by pressing confirm. The user is then asked to confirm that he/she is ready for filling of the balloon. However, both said confirmation steps may be omitted, in which case the process immediately proceeds to the next step, without requesting confirmation.

Filling of the balloon is preferably made to one of a few predetermined filling levels, in accordance with the method discussed above with reference to FIG. 4. Here, in step S13, pressing of the increase button once may start an automatic procedure, wherein the balloon is automatically inflated until one of the thresholds has been reached, whereby the pumping is immediately aborted by the controller. However, alternative ways of filling the balloon are feasible. For example, the filling may be performed continuously while the increase button is depressed, as long as neither of the thresholds has been reached.

In a further step, S14, the user is requested to confirm that he/she is now ready for irrigation. In this stage, continuous depression of the confirmation button is requested. The progress of the irrigation may be indicated on the display, as a progress bar, indication of volume that has been pumped or is remaining, time left, etc. If it is determined, step S15, that the confirmation button has been released prior to completion of the irrigation, the process is brought back to step S12 as a safety measure. Hereby, the activation of the pump functions as a "dead man's handle", so that irrigation will immediately be aborted if something unintentional occurs.

If the irrigation process is not aborted, the irrigation continues until the predetermined volume of irrigation liquid has been discharged. When irrigation has been completed, step S16, the user is asked to deflate the balloon by pressing decrease. When this has been done, and the probe has been removed, the user is asked to dry the system, step S17, by pressing confirm, whereby remaining irrigation liquid in the tubing is pumped out. Then, the control unit may be powered off, and the irrigation is completed, step S18.

The above-discussed irrigation process can naturally be varied in many ways, as would be apparent for the skilled addressee. For example, several of the steps may be omitted, combined or executed in a different order. For example, several of the confirmation steps may be omitted, so that the procedure can perform several of the steps automatically, without requesting confirmation from the user. The initiation/parameter setting stage may also be omitted in the default procedure, and instead being separately accessible upon request. This is e.g. of advantage in applications were parameter settings are to be made primarily by a physician or the like, and where the user is normally not intended to alter the parameter settings. However, additional steps of confirmation, parameter setting and the like may also be added to the process.

As a further illustration of the variations in procedural steps which are feasible, another embodiment illustrating a process involving fewer steps is will now be discussed with reference to FIG. 7. In order to simplify understanding, the same or similar steps as discussed above in relation to FIG. 6 are assigned the same or similar reference denominations.

In a first step S1, the control unit is activated.

Following activation, the process immediately proceeds to a priming step S10'. Priming may e.g. comprise pumping of irrigation to fill the tubing with liquid, etc. At this stage, the probe may remain in its package. If the probe is provided with a hydrophilic coating, irrigation liquid may also be pumped to ensure that the hydrophilic coating is properly wetted and activated. As in the previous embodiment, the confirmation step may be omitted.

When priming is completed, the user is asked, in step S11, to insert the probe in the operational position. When this has been done, this is confirmed by pressing confirm. As in the previous embodiment, the confirmation step may be omitted.

Next to follow is a balloon inflation/deflation step S12'. This step may be identical to the balloon inflation/deflation described previously in relation to FIG. 6. Here, the balloon is continuously inflated when the increase button is depressed. Further, filling of the balloon is preferably immediately aborted as soon as the button ceases to be depressed, and also when either of the thresholds corresponding to the selected inflation level has been reached. Similarly, the balloon is continuously deflated when the increase button is depressed. Further, deflation of the balloon is preferably immediately aborted as soon as the button ceases to be depressed. Hereby, the user can easily inflate the balloon to a desired level by keeping the increase button depressed until a desired filling level has been obtained, and thereafter release the button.

In this step S14', depression of the confirmation button, or alternatively the increase button, activates pumping of the irrigation liquid through the catheter. The progress of the irrigation may be indicated on the display, as a progress bar, indication of volume that has been pumped or is remaining, time left, etc. Pumping continues as long as the button continues to be depressed. However, as soon as the button is released, pumping is immediately aborted, in analogy to what has been discussed previously. Hereby, the activation of the pump functions as a "dead man's handle", so that irrigation will immediately be aborted if something unintentional occurs. Pumping may also optionally be automatically aborted, despite depression of the button, if it is determined that the reservoir holding the irrigation liquid has been emptied. Pumping may also optionally be automatically aborted, despite depression of the button, when it is determined that a predetermined irrigation volume has been irrigated.

When pumping has been stopped or aborted, the process may proceed to step S15', in which the user is informed that pumping has been aborted, and/or the level of balloon inflation is presented. Other information may also be presented to the user in this step. Further, this step may also be omitted.

After a predetermined time, or after confirmation by the user, e.g. by depressing the confirm button, or alternatively immediately after abortion of pumping of the irrigation liquid (in case step S15' is omitted), the process returns to step S12'. Here, the user may re-adjust the filling level of the balloon, as described previously, by using the increase and decrease buttons. The user may also confirm that the balloon pressure is satisfactory, and again proceed to the irrigation step S14' by depressing the confirm button. However, if it is or has been determined that the reservoir holding the irrigation liquid has been emptied and/or that a predetermined irrigation volume has been irrigated, proceeding to step S14' may optionally be hindered.

In step S12', the balloon may further be deflated for withdrawal of the catheter, after completed irrigation or when a user wishes to abort the procedure prior to completeness. Deflation is accomplished by continuous depression of the decrease button. When the balloon has been deflated, the user confirms this by depression of the confirm button, and the process then ends in step S18.

The irrigation process may, however, be even further simplified. In a very simple process, the irrigation system is operated in the following way:

The irrigation system is turned on.
The irrigation system is operated to pump irrigation liquid through the probe for priming.
The probe is inserted in operative position in the user.
The inflatable retention member is inflated so that a predetermined filling level is achieved.
Irrigation liquid is pumped until a predetermined total volume has been pumped.
The inflatable retention member is deflated.
The process is ended.

Figure 7:
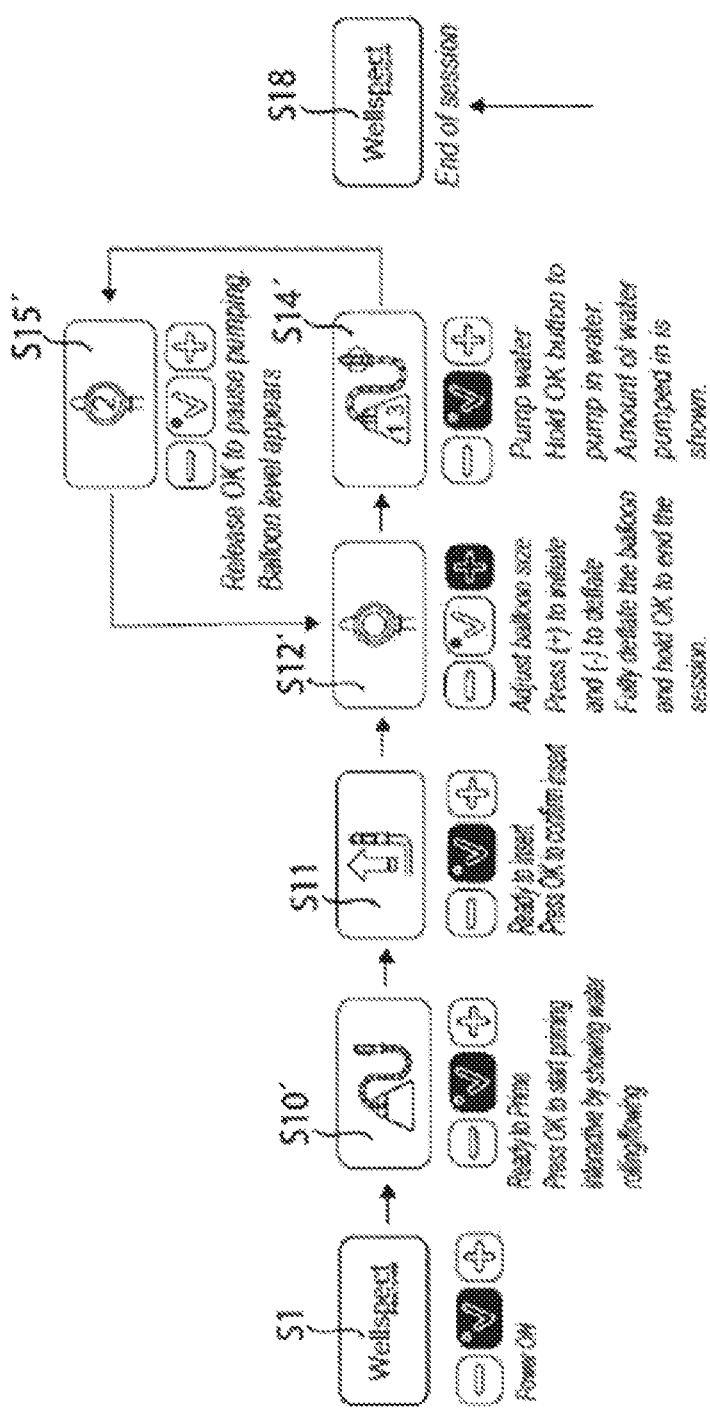
FIG. 7 is a schematic overview of the steps of an alternative embodiment of an irrigation procedure using an irrigation system.

Even in the simplified procedure discussed above, or the in the simplified procedure discussed in relation to FIG. 7, a parameter setting mode or the like is provided, to select an inflation level, and also e.g. to determine a predetermined irrigation volume to be used for irrigation, to adjust the pumping speed for inflating/deflating the balloon and/or for pumping the irrigation liquid, etc. The parameter setting mode may be entered by simultaneous depression of two or more of the control buttons, by activation of a further control button, by connecting the control unit to an external device, or the like.

Thus a desired flow rate may be set and input by the user in various ways prior to irrigation, e.g. in a parameter setting mode as discussed above. However, the desired flow rate may also be input in other ways, such as via a remote control or the like.

Further, it is also possible to allow the desired flow rate to be adjusted during the irrigation procedure. For example, it is possible to use switches for pumping also sensing the pressure level being applied by the user to the control element, and to adapt e.g. the desired flow rate value in accordance with the determined pressure level. For example during the irrigation step S14 or S14', it may be determined if the applied pressure to the confirm button is exceeding a certain threshold level, and if so use a higher flow rate value, and if not, to use a lower flow rate value. More than two low rate values may also be provided. Pumping may also optionally be automatically aborted, despite depression of the button, if it is determined that the reservoir holding the irrigation liquid has been emptied.

Further, the desired flow rate may be varied in direct correlation to the applied pressure.

Alternatively, the user may be given the opportunity of determining the desired flow rate directly by provision of two or more dedicated control buttons related to "increase", "decrease" and "confirm". The user may then select whether to use the high or low flow rate for a certain action, and may also use these buttons to adjust the desired flow rate during use.

The person skilled in the art realizes that the present invention is not limited to the preferred embodiments. For example, many ways of selecting a desired inflation level are feasible. Further, the control elements may be realized in many different ways, such as mechanical control buttons, galvanically isolated touch buttons, areas on a touch screen and the like. The control elements may also, additionally or alternatively, be arranged on a remote control. Also, many types of electrically operable valve may be used for the flow rate control.

Such and other obvious modifications must be considered to be within the scope of the present invention. It should be noted that the above-mentioned embodiments illustrate rather than limit the invention, and that those skilled in the art will be able to design many alternative embodiments without departing from the scope of the appended claims. In the claims, any reference signs placed between parentheses shall not be construed as limiting to the claim. The word "comprising" does not exclude the presence of other elements or steps than those listed in the claim. The word "a" or "an" preceding an element does not exclude the presence of a plurality of such elements. Further, a single unit may perform the functions of several means recited in the claims.

The invention claimed is:

1. A method for automated control of inflation of an inflatable retention member in a catheter by a controller, said method comprising:
   providing a plurality of predetermined inflation levels;
   providing, for each of said predetermined inflation levels, a pumping time threshold and a pressure level threshold;
   continuously measuring the pressure in said inflatable retention member;
   receiving input of a selected inflation level selected form said plurality of inflation levels; and
   operating an electric pump to inflate said inflatable retention member;
   wherein said operating of the electric pump is continued until one of the pumping time threshold or pressure level threshold of said selected inflation level has been reached.

2. The method of claim 1, wherein the plurality of predetermined inflation levels comprises at least 3 different inflation levels.

3. The method of claim 1, wherein the plurality of predetermined inflation levels ranges from a lowest inflation level to a highest inflation level, and wherein the pumping time threshold and the pressure level threshold both increase incrementally between each predetermined inflation level from the lowest inflation level to the highest inflation level.

4. The method of claim 1, wherein the pumping time thresholds are all within the range 0.1-60 seconds.

5. The method of claim 1, wherein the pumping time threshold is compared to a monitored total pumping time, the total pumping time comprising the times during which the pump has been active, but disregarding times when the pump has been idle.

6. The method of claim 5, wherein during deflation, the monitored total pumping time is reduced with a time corresponding to the time it will take for the pump to re-inflate the inflatable retention member to the same size as prior to deflation.

7. The method of claim 1, further comprising the steps of continuing to monitor the pressure level and the pumping time during use of the catheter, and to continue inflation of the inflatable retention member when both the pressure is below the pressure level threshold and the pumping time is below the pumping time threshold, and to deflate the inflatable retention member when either of the thresholds are exceeded or exceeded by a predetermined value.

8. The method of claim 1, wherein the pressure level thresholds are all within the range 1-500 mbar.

9. The method of claim 1, wherein the continuous measuring of the pressure in the inflatable retention member is made by a pressure sensor arranged directly in the inflatable retention member, or in conduit being in direct communication with the inflatable retention member.

10. A catheter system, comprising:
    a catheter having an inflatable retention member;
    an electric pump for pumping a fluid for inflation of said inflatable retention member;
    a pressure sensor continuously sensing the pressure in the inflatable retention member;
    a controller for automated control of said electric pump, the controller comprising a memory storing a set of inflation levels, each level being correlated to a pressure level threshold and pumping time threshold; and
    a user interface arranged to receive input of a selected inflation level selected form a plurality of predetermined inflation levels;
    wherein the controller is arranged to operate the electric pump until one of the pumping time threshold and pressure level threshold of said selected inflation level has been reached.

11. The system of claim 10, wherein the catheter is a rectal catheter, and wherein the catheter system is an irrigation system, said system further comprising:
    a reservoir for an irrigating liquid;
    tubing providing fluid communication between said reservoir and said catheter; and
    an electrical pump for indirectly pumping irrigation liquid from the reservoir to the probe through said tubing, wherein said electrical pump is either the same as the electric pump for pumping a fluid for inflation of the inflatable retention member, or a second pump.

12. The system of claim 10, wherein the plurality of predetermined inflation levels ranges from a lowest inflation level to a highest inflation level, and wherein the pumping time threshold and the pressure level threshold both increase incrementally between each predetermined inflation level from the lowest inflation level to the highest inflation level.

13. The system of claim 10, further comprising a control unit with a housing, said housing enclosing said controller, said electric pump, and said pressure sensor.

14. The system of claim 13, wherein the control unit is further provided with a display and said user interface to receive input of a selected inflation level.

15. The system of claim 13, wherein the tubing includes a first part connecting the control unit with the probe and a second part connecting the reservoir with the control unit, and in which each of said first and second parts comprises a gas conducting tube and an irrigating liquid conducting tube.

16. The system of claim 10, further comprising a safety element, being separate from the controller and being connected to the pressure sensor, whereby the safety element is arranged to stop the pump when the sensed pressure in the inflatable retention member reaches or exceeds a predetermined maximum safety value.

17. The catheter of claim 10, wherein the catheter system is a rectal or stomal irrigation catheter system.

* * * * *